United States Patent [19] [11] 3,997,293
Redmore [45] Dec. 14, 1976

[54] USE OF DIHYDRO-NITROGEN HETEROCYCLIC PHOSPHORAMIDATES AS CORROSION INHIBITORS

[75] Inventor: Derek Redmore, Ballwin, Mo.

[73] Assignee: Petrolite Corporation, St. Louis, Mo.

[22] Filed: Aug. 7, 1975

[21] Appl. No.: 602,634

Related U.S. Application Data

[62] Division of Ser. No. 453,013, March 19, 1974, Pat. No. 3,923,490, which is a division of Ser. No. 210,106, Dec. 20, 1971, Pat. No. 3,821,232.

[52] U.S. Cl. .............................. 21/2.5 A; 21/2.7 A; 252/8.5 C; 252/8.55 C; 252/8.55 D; 252/8.55 E; 252/147; 252/389 A
[51] Int. Cl.² .................. C23F 11/00; C23F 11/04; C23F 11/10; C23G 1/06
[58] Field of Search ................. 252/8.55 E, 8.55 C, 252/148, 389 A, 8.5 C, 8.55 D, 147; 21/2.5 A, 2.7 A

[56] References Cited
UNITED STATES PATENTS

| | | | |
|---|---|---|---|
| 2,468,163 | 1/1948 | Blair et al. | 252/8.55 |
| 3,524,908 | 8/1970 | Redmore | 252/8.55 X |
| 3,720,498 | 3/1973 | Redmore | 21/2.5 |
| 3,821,232 | 6/1974 | Redmore | 252/390 X |
| 3,923,490 | 12/1975 | Redmore | 71/67 |

*Primary Examiner*—Herbert B. Guynn
*Attorney, Agent, or Firm*—Sidney B. Ring; Hyman F. Glass

[57] ABSTRACT

Dihydro-nitrogen heterocyclic phosphoramidates of the general formula

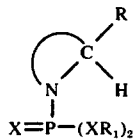

where N — C represents a dihydro-nitrogen ring, R is a substituted group, preferably hydrocarbon, X is O or S, and $R_1$ is an alcohol or phenolic moiety, preferably hydrocarbon; the preparation and uses thereof particularly as corrosion inhibitors, microbiocides, etc.

12 Claims, No Drawings

USE OF DIHYDRO-NITROGEN HETEROCYCLIC PHOSPHORAMIDATES AS CORROSION INHIBITORS

This application is a division of Ser. No. 453,013 filed Mar. 19, 1974, now U.S. Pat. No. 3,923,490, which is a division of Ser. No. 210,106 filed Dec. 20, 1971, now U.S. Pat. No. 3,821,232.

This invention relates to dihydro-nitrogen heterocyclic phosphoramidates characterized by the formula

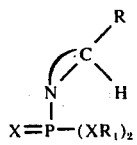

where R is a substituted group and $R_1$ is an alcohol moiety, where R and $R_1$ are alkyl as lower alkyl, aryl, cycloalkyl, alkaryl, aralkyl, etc., X is oxygen or sulfur, and the circle represents a cyclic structure which may be a sole cyclic structure or attached to other cyclic groups. Representative compounds include

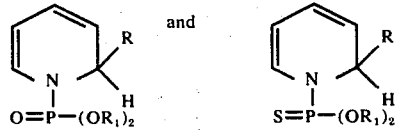

where R and $R_1$ are alkyl, aryl, etc.

These compounds are prepared by reacting nitrogen heterocyclics in a hydrocarbon metal or Grignard type reaction for example, according to the following reactions

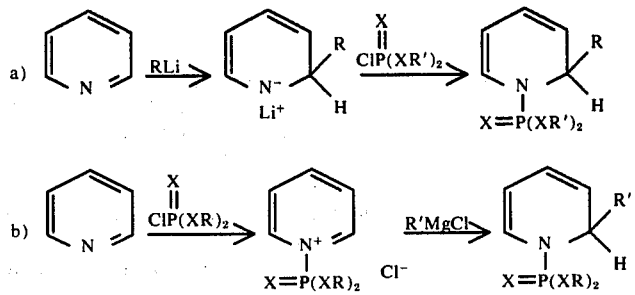

These products have a wide variety of uses including their use as corrosion inhibitors, biocides, etc. Derivatives of these products can also be prepared, such as the Diels-Alder Adduct, etc.

Any nitrogen heterocyclic capable of being activated so as to react with a phosphochloridate can be reacted. These include heterocyclics having one or more rings where at least one ring has a nitrogen heterocyclic group and the other rings are carbocyclic or heterocyclic, i.e.; they may contain oxygen or other non-carbon elements in the ring, etc.

They may be illustrated by the formula

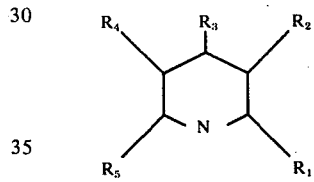

where the R's, which may or may not be the same, are hydrogen or a substituted group, for example, alkyl, cycloalkyl, aryl, aralkyl, alkoxy, halo, etc. The R's may also be further substituted provided the substituted groups do not interfere with the reaction.

An R group may also be joined to an adjacent group so as to form a ring provided ortho and/or para positions are available for substitution, for example in the following aromatic type ring systems:

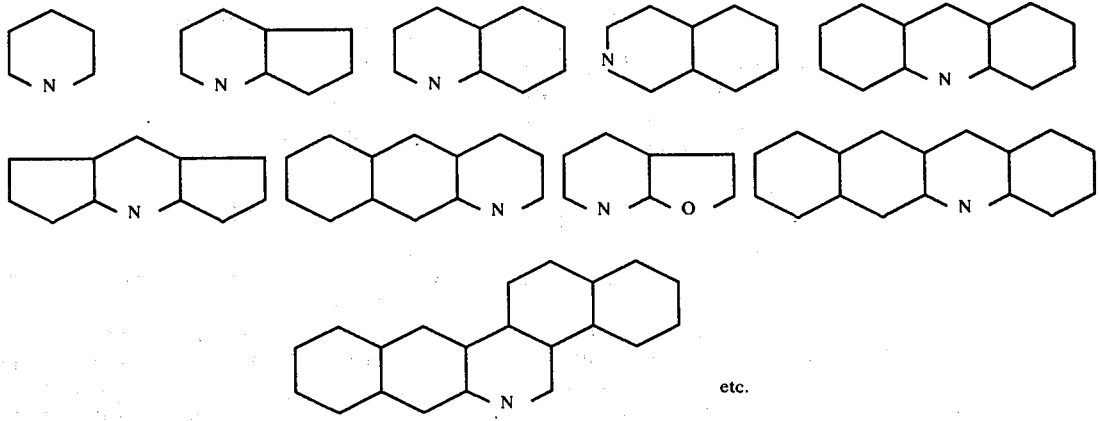

etc.

The above ring systems may also be substituted. The adjacent rings may also contain heterocyclic groups for example oxygen, nitrogen, etc., and/or may contain rings having less than 6 molecules in the ring for example a 5 member ring.

In certain instances more than one nitrogen heterocyclic ring may be capable of reacting with the phosphochloridate so that substitution may occur in more than one ring.

Representative examples of heterocyclic reactants include pyridines and benzo- and dibenzo- derivatives of pyridine, for example, pyridine, alkylated pyridines such as 2-picoline, 3-picoline, 4-picoline, etc., 2,4-lutidine, 2,6-lutidine, 2,3-lutidine, etc., collidines, etc., quinoline and alkylated quinolines, etc., isoquinolines, and alkylated isoquinolines, etc., phenanthridines, and substituted phenanthridines, etc., acridines and substituted acridines, etc.

By means of the present reaction, the chloridate moiety of a phosphite group is added to the nitrogen atoms in the form of the phosphite ester to form an amide

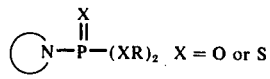

The phosphorus reactant in this reaction is a diester acid halide of a phosphoric or thio-phosphoric acid,

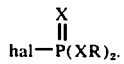

The X can be oxygen or sulfur, for example

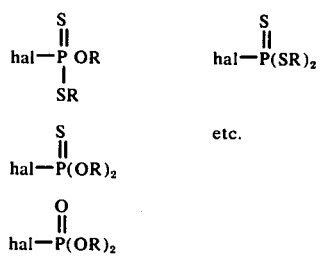

R can be alkyl, cycloalkyl, aralkyl, aryl, etc., such as methyl, ethyl, propyl, cyclohexyl, phenyl, etc.

The reaction is preferably carried out in an inert solvent such as hexane, benzene, tetrahydrofuran, dioxane, etc., at temperatures from −70° to +100° C., but preferably from −20° to +20° C.

The organometallic reagent can be an alkali metal alkyl or aryl derivative such as butyl lithium, methyl lithium, phenyl lithium, or a Grignard reagent such as methyl magnesium chloride, phenyl magnesium bromide, etc.

The preparation of the dihydro-nitrogen heterocyclic phosphoramidate can be carried out in two ways both of which involve two steps. The nitrogen heterocylic compound can be reacted with the organometallic reagent to form an intermediate which is then reacted with the phosphorus reagent. The second method involves reaction of the heterocyclic compound with the phosphorus reagent followed by treatment with the organometallic reagent. Although in some cases it is possible to form the dihydro-nitrogen heterocyclic phosphoramidates by mixing all three reagents, it is usually preferred to use either of the two step-wise reaction procedures.

These procedures are illustrated in the following examples. The following examples are presented by way of illustration and not of limitation.

EXAMPLE 1

To a 2.2M solution of phenyl lithium in benzene-ether (114 ml; 0.25 mole) cooled to 0° was added a solution of pyridine (20 g; 0.25 mole) in ether (50 ml) at 0°–5° during 1 hour. After stirring for 1 hour at 0° the resulting blood-red solution was added to diethyl phosphorochloridate (43.3 g; 0.25 mole) in ether (50 ml) during 80 minutes at 5°–10° with cooling. The resulting pale yellow solution was stirred overnight at room temperature and water (100 ml) was added. The organic phase was separated and evaporated to yield crude dihydropyridine. Distillation yielded the pure dihydropyridine (30 g) bp 115°–130°/0.04 mm. The NMR spectrum and infrared spectrum showed the expected absorptions for the following structure:

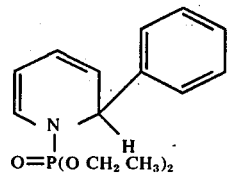

Analysis calculated for $C_{15}H_{20}NO_3P$, N, 4.78; P, 10.58%; Found: N, 4.92; P, 10.50.

EXAMPLE 2

To a 23% solution of butyl lithium in hexane (69 g; 0.23 mole) cooled to −20° was added pyridine (18.5 g; 0.23 mole) in ether (100 ml) during 30 minutes. After warming to 0° and stirring at this temperature for 1 hour diethyl phosphorochloridate (40.5 g; 0.23 mole) in ether (100 ml) was added during 30 minutes at 0° – 10°. The resulting pale yellow solution was stirred at room temperature overnight and water (200 ml) added. The organic layer was separated and solvent removed by distillation. Distillation of the residue yielded the dihydropyridine (24.2 g) bp 96°– 110°/0.25 mm. The NMR and infrared spectra were consistent only with the dihydropyridine structure below:

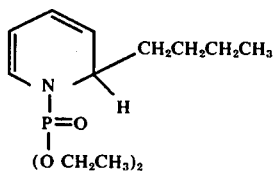

EXAMPLE 3

3,5-dimethylpyridine (37 g; 0.35 mole) was added dropwise to a 2.3 M solution of phenyl lithium (155 ml; 0.35 mole) in benzene/ether at 2° – 6° during 45 minutes. After allowing the mixture to warm to 15° it was added in 90 minutes to a solution of diethyl phosphorochloridate (60.9 g; 0.35 mole) in ether (200 ml) at 5° – 15°. After stirring overnight the work-up procedure of Example 1 was employed. Distillation yielded the dihydropyridine (58 g) bp 110° – 120°/0.1 mm. The NMR and IR spectra were consistent only with the following dihydropyridine structure:

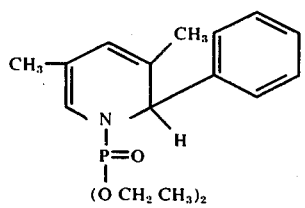

EXAMPLE 4

To a solution of pyridine (21.3 g; 0.27 mole) in ether cooled and stirred at −70° was added a 1.6 M solution of butyl lithium in hexane (170 ml; 0.27 mole) during 10 minutes. The solution was allowed to warm to 0° and stirred at this temperature for one hour. The resulting solution was then added at 10° − 20° to dimethyl thionophosphoro chloridate (43.3 g; 0.27 mole) in ether (100 ml) in 1 hour. After stirring overnight water (100 ml) was added and the organic layer separated. Evaporation of the solvent yielded the crude dihydropyridine which upon distillation yielded pure product, bp 85° − 95°/0.2 mm, represented by the following formula:

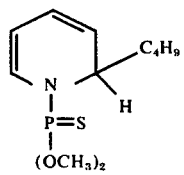

The following compounds were prepared using similar procedures:

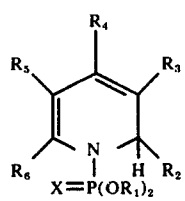

| Ex. | $R_1$ | $R_2$ | $R_3$ | $R_4$ | $R_5$ | $R_6$ | X |
|---|---|---|---|---|---|---|---|
| 5 | $C_2H_5$ | $C_4H_9$ | H | $CH_3$ | H | H | O |
| 6 | $C_2H_5$ | $C_4H_9$ | H | H | H | $CH_3$ | O |
| 7 | $CH_3$ | $C_4H_9$ | H | $CH_3$ | H | H | S |
| 8 | $C_2H_5$ | $C_6H_5$ | H | $CH_3$ | H | H | S |
| 9 | $C_2H_5$ | $C_6H_5$ | H | H | H | H | S |
| 10 | $C_4H_9$ | $C_6H_5$ | H | $CH_3$ | H | $CH_3$ | O |
| 11 | $C_2H_5$ | $C_6H_5$ | H | $CH_3$ | H | $CH_3$ | S |

The following examples illustrate the use of an alternative procedure for the preparation of N-phosphorus substituted 1,2-dihydropyridines.

EXAMPLE 12

Pyridine (7 g; 0.09 mole) was added at 15° − 20° to a solution of diethyl phosphorochloridate (15.3 g; 0.09 mole) in benzene (60 ml). After stirring the resulting slurry for 1 hour, methyl magnesium chloride (0.09 mole) in tetrahydrofuran was added at 5° − 10° in 1 hour. After stirring 1 hour at 10° − 25° water (50 ml) was added and the organic phase separated. Distillation gave pure dihydropyridine, bp 85°−89°/0.1 mm. The NMR and IR spectra were consistent only with the following structure:

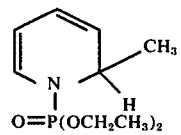

By the method of Example 12 additional dihydropyridines were prepared as follows:

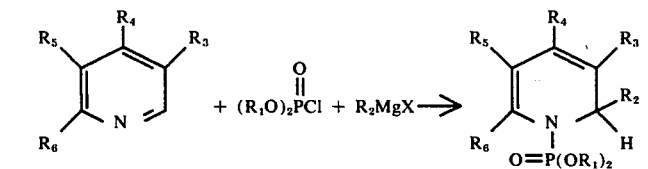

| Ex. | $R_1$ | $R_2$ | $R_3$ | $R_4$ | $R_5$ | $R_6$ |
|---|---|---|---|---|---|---|
| 13 | Et | Ph | H | H | H | H |
| 14 | Et | Ph | H | $CH_3$ | H | H |
| 15 | iso-Pr | Me | H | H | H | H |
| 16 | iso-Pr | Me | Me | H | H | H |
| 17 | Et | Me | Me | H | Me | H |
| 18 | iso-Pr | Me | Me | H | Me | H |

The dihydroheterocyclic phosphoramidates of this invention act as a conjugated diene system that can be reacted with a dienophile to form the Diels Alder Reaction product. These are illustrated by the following reaction:

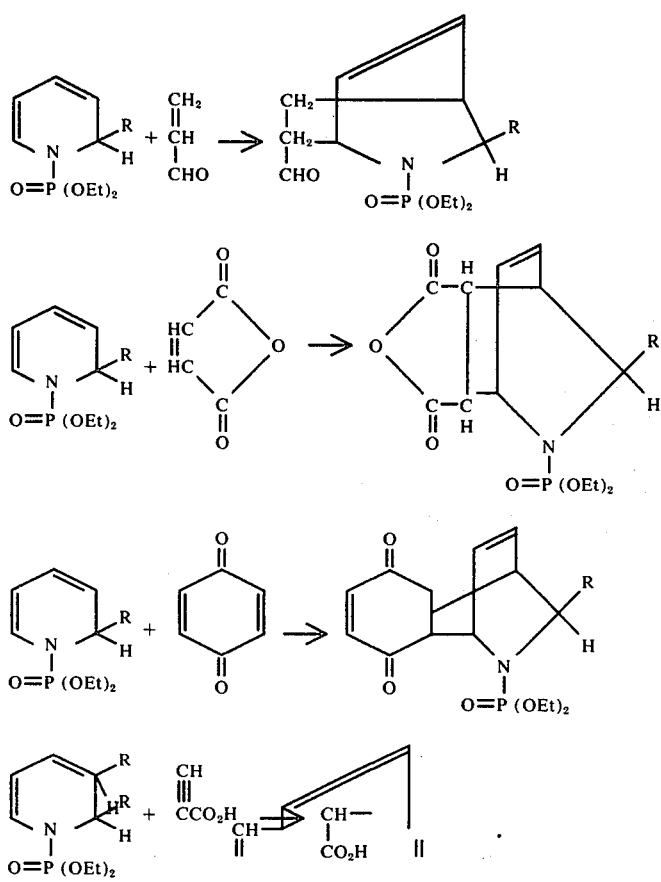

The following present certain categories of dienophiles which can react with the compositions of this invention.
1. $CH_2 = CHA$.
   A = CHO, $CO_2H$, $CO_2CH_3$, $CO_2C_2H_5$, COCl, $COCH_3$, $COC_6H_5$, CN, $NO_2$, $C_6H_5$, $CH_2OH$, $CH_2X$, $CH_2NH_2$, $CH_2CN$, $CH_2CO_2H$, $CH_2NCS$, $OCOCH_3$, $SC_6H_4CH_3$, $SO_2R$, X, H.
2. $C_6H_5CH = CHA$.
   A = CHO, $CO_2H$, $CO_2CH_3$, $CO_2C_2H_5$, $COCH_3$, $COC_6H_5$.
3. $CH_2 = CA_2$.
   A = $CO_2C_2H_5$, CN, $COCH_3$, X.
4. ACH = CHA.
   A = $CO_2H$, COCl, $CO_2CH_3$, $CO_2C_2H_5$, $COCH_3$, $COC_6H_5$, X.
5. Quinones.
6. AC ≡ CA.
   A = $CO_2H$, $CO_2CH_3$, $CO_2C_2H_5$, $COC_6H_5$, $C_6H_5$, H.

The more reactive dienophiles usually contain the C = C — C = O or the C ≡ C — C = O system. Other unsaturated groups, such as CN, $NO_2$, or $SO_2$, promote the addition. In some instances even substances with isolated double bonds have been found to add dienes, but these substances usually require more drastic reaction conditions.

Among those substances that have been employed most frequently as dienophiles are maleic anhydride and other closely related dicarboxylic acid derivatives, alpha, beta-unsaturated carbonyl compounds and acetylenic compounds and quinones and other cyclic ketones.

The following Table lists specific dienophiles.
Acrolein
Crotonaldehyde
Cinnamaldehyde
Acetylethylene (methyl vinyl ketone)
Ethylideneacetone
Benzoylethylene (vinyl phenyl ketone)
Benzalacetone and benzalacetophenone
Dibenzalacetone
1-Cyclopenten-3-one and derivatives
1-Cyclohexen-3-one
sym-Dicetylethylene
sym-Diaroylethylenes
Acrylic acids
Crotonic acid and crotonyl chloride
Cinnamic acids and esters
3,4-Dihydro-1-naphthoic acids and esters
Coumarin
Beta-Aroylacrylic acids
Alkylidene-malonic, -acetoacetic, and -cyanoacetic esters
Ethylenetetracarboxylic acid and ester
Azoidcarboxylic ester
Acrylonitrile
Beta-Naphthol (keto tautomer)
Nitroalkenes
Alpha-Beta-Unsaturated sulfones
Cyclopentadiene
1,3-Cyclohexadiene
Styrene
Indenes
Acenaphthylene Allyl compounds
Vinyl halides, esters, and sulfides
Di- and poly-chloroethylenes
4-Vinyl-1cyclohexene
1-Methyl-1-cyclopentene
Unsaturated bicyclic compounds (such as dicyclopentadiene)
Ethylene The following examples illustrate the formation of Diels-Alder adducts:

EXAMPLE 19

The product of Example 1 (3.1 g) was warmed in benzene (30 ml) with maleic anhydride (1.05 g) at 80° for 1 hour. Evaporation of the solvent yielded a gum which afforded white crystals mp 145°–8° from benzene/hexane of the bicyclo octyl derivative.

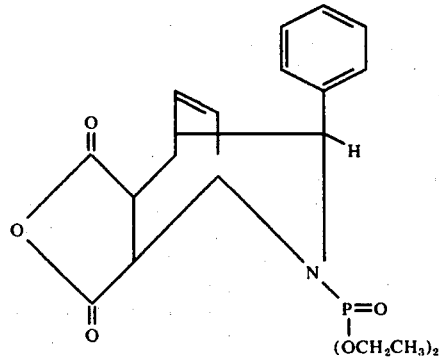

EXAMPLE 20

The dihydropyridine of Example 3 (6 g) was heated in benzene (25 ml) with N-phenyl maleimide (3 g) at 80° for 30 minutes. Evaporation of the solvent gave a gum from which crystals were obtained using benzene/hexane solvent, mp 93°–5°.

Analysis: Calculated for $C_{27}H_{31}N_2O_5P \cdot \frac{1}{2}C_6H_6$; C, 67.42; H, 6.37; N, 5.24; P, 5.81. Found: C, 67.23; H, 6.53; N, 5.32; P. 5.91.

The structure of the product is represented as follows:

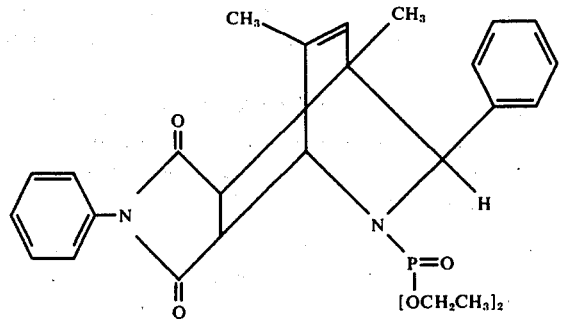

The Diels-Alder adducts may also be employed as microbiocides, corrosion inhibitors, etc.

USE AS A MICROBIOCIDE

I. IN WATER TREATMENT

This phase of the present invention relates to the treatment of water. More particularly, it is directed to providing improved means for controlling microbiological organisms including bacteria, fungi, algae, protozoa, and the like, present in water.

It is well known that ordinary water contains various bacteria, fungi, algae, protozoa and other microbiological organisms which, if uncontrolled, multiply under certain conditions so as to present many serious problems. For example, in swimming pools the growth of these microbiological organisms is very undesirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, as well as many other costly and deleterious effects.

In other industrial applications where water is used in processes, as for example, as a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplies, in cooling towers, air-conditioning systems, on the farm and ranch, in the factory, in civilian and military hospitals and dispensaries, in camps, for swimming pools, baths and aquaria, waterworks, wells, reservoirs, by fire-fighting agencies, on maritime and naval vessels, in boilers, steam-generators and locomotives, in pulp and paper mills, for irrigation and drainage, for sewage and waste disposal, in the textile industry, in the chemical industries, in the tanning industry, et cetera, and which will render said water supplies bactericidal, fungicidal and algicidal. They further provide a simple process whereby water supplies, for whatever purposes intended, are rendered bacteriostatic, fungistatic and algistatic, i.e., said water supplies treated by the process of this invention will resist and inhibit the further growth or proliferation of bacteria, fungi, algae and all forms of microbial life therein.

The compositions of this invention can be employed in concentrations of from about 5 ppm, such as about 5 to 10,000 ppm, for example from about 10 to 1,000 ppm, but preferably from about 25 to 250 ppm. In general, a concentration sufficient to obtain a desired result is employed.

II. WATER FLOODING IN SECONDARY RECOVERY OF OIL

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding taking place in the presence of sulfate-reducing bacteria.

Water flooding is widely used in the petroleum industry to effect secondary recovery of oil. By employing this process the yield of oil from a given field may be increased beyond the 20 – 30 percent of the oil in a producing formation that is usually recovered in the primary process. In flooding operations, water is forced under pressure through injection wells into or under oil-bearing formations to displace the oil therefrom to adjacent producing wells. The oil-water mixture is usually pumped from the producing wells into a receiving tank where the water, separated from the oil, is siphoned off, and the oil then transferred to storage tanks. It is desirable in carrying out this process to maintain a high rate of water injection with a minimum expenditure of energy. Any impediment to the free entry of water into oil bearing formations seriously reduces the efficiency of the recovery operation.

The term "flood water" as herein employed is any water injected into oil-bearing formations for the secondary recovery of oil. In conventional operations, the water employed varies from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and/or existing in sufficiently high numbers to constitute an appreciable mass, thereby plugging the pores of the oil-bearing formation. Pore-plugging increases the pressure necessary to drive a given volume of water into an oil-bearing formation and oftentimes causes the flooding water to by-pass the formation to be flooded. In addition, microorganisms may bring about corrosion by acting on the metal structures of the wells involved, producing corrosive substances such as hydrogen sulfide, or producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

Organisms of the Desulfovibrio genus, more commonly known as sulfate reducing bacteria, are known particularly to preclude efficient operation of oil recovery by conventional water flooding techniques by producing $H_2S$ which reacts with iron or iron salts to precipitate black ferrous sulfide. These organisms are often resistant to the effects of many known antimicrobial compounds.

I have discovered that the compositions of this invention are effective bactericides for sulfate reducing bacteria.

III. HYDROCARBON TREATMENT

This phase of the present invention relates to the use of these compounds as biocides in hydrocarbon systems.

In addition to being used as biocides in aqueous systems, the compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product; that microorganisms cause the formation of gums, $H_2S$, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

The compositions of this invention can be employed in hydrocarbon systems.

MICROBIOCIDAL TESTING

The procedure was carried out in the following manner. Solutions of test compounds were aseptically added to a sterile broth which would support growth of the following test organisms:
1. Sulfate reducing bacteria
2. Aerobic bacteria Growth media prescribed by the American Petroleum Institute was used. The broth containing the test compound was dispersed into sterile disposable tubes and the tubes were inoculated with the growing organisms and incubated at 35° C for 24 hours. The absence or presence of growth was determined by visual inspection by an experienced observer.

The compositions of this disclosure show good biocidal activity in both aerobic systems and against sulfate reducing bacteria as illustrated in the following table.

| Compound | Concentration for 100% kill against sulfate reducing bacteria | | |
| --- | --- | --- | --- |
| Example 3 | 30 ppm | | |
| Example 4 | 30 ppm | | |
| Example 19 | 30 ppm | | |
| | Aerobic Bacteria % kill at | | |
| | 25 ppm | 50 ppm | 100 ppm |
| Example 3 | 60% | 85% | 90% |
| Example 1 | 70% | 80% | 90% |
| Example 17 | 88% | 92% | 95% |
| Example 19 | 92% | 96% | 98% |

The compounds of this invention are particularly useful as corrosion inhibitors, particularly in acidic systems.

USE IN FLUIDS FOR DRILLING WELLS

This phase of the invention relates to the use of the compounds of this invention as corrosion inhibitors in producing an improved drilling fluid useful in drilling oil and gas wells.

Fluids commonly used for the drilling of oil and gas wells are of two general types: water-base drilling fluids comprising, for example, a clay suspended in water, and oil-base drilling fluids comprising, for example, a clay or calcium carbonate suspended in mineral oil.

A third type of drilling fluid which has recently been developed, is one of oil-in-water or water-in-oil emulsion, for example, emulsions of mineral oil in water or water in mineral oil formed by means of emulsifiers such as fulfuric acid; Turkey-red oil; soaps of fatty acids, for example, sodium oleate; emulsoid colloids, for example, starch, sodium alginate, etc. Varying amounts of finely divided clay, silica, calcium carbonate, blown asphalt and other materials may be added to these emulsions to improve their properties and control their weight.

I have now discovered that the compositions of this invention can be employed as a corrosion inhibitor in drilling fluids.

USE IN AIR DRILLING

It has long been conventional practice in drilling deep bore holes to circulate a drilling mud down through the drill stem and up through the bore hole between the wall of the bore hole and the drill stem for the removal of chips or cuttings from the bore hole and to provide support for the wall of the bore hole. More recently, in the drilling of holes in which wall support provided by drilling mud is not employed, drilling has been carried out with the use of air for chip removal. Such drilling is not only normally faster than mud drilling but is indispensable in areas where the supply of water is limited or when drilling through cavernous formations into which the drilling mud flows and becomes lost.

The increasing popularity of air or gas drilling has come about not only because this method of drilling is frequently faster, as noted above, but for the additional reasons that the drill bits last longer, the provision and handling of water under wide ranges of temperature conditions is avoided, boring samples are easily observed when they are not mixed with mud, and there is no loss involved as in the case of mud drilling when drilling through cavernous formations. Furthermore, prompt removal of water entering the hole maintains a dry hole and the likelihood of wall collapse is thereby reduced.

In a typical air drilling operation there may be provided, for example, an up-flow of air in the bore hole having a velocity of the order of 3,000 feet per minute. This flow of air upwardly through the bore hole, which is produced by air pumped downwardly through the drill stem, provides adequate removal of cuttings. The air is delivered to the drill stem at pressures of 20 to 60 lbs. per square inch and for dewatering or for breaking obstructions, as will be hereinafter described, the pressures may be increased to 180 to 200 lbs. or more per square inch.

Air drilling operations are frequently hampered by the inflow of water into the bore hole when the drill bit is penetrating a water bearing stratum or when the bore hole has passed through a water bearing stratum that has not been cased. Normally, if drilling proceeds uninterruptedly both before and during penetration into a water bearing stratum, the flow of air is sufficient to blow the water out of the bore hole along with the cuttings and drilling dirt. There are, however, two major problems encountered in air drilling when water is entering the bore hole. The first problem occurs when there is a small inflow of water sufficient to cause a dampening of the cuttings which, under certain conditions, will then ball-up, clogging and sometimes jamming the drill bit. The second problem is encountered when there is a substantial amount of water remaining in the bottom of the bore hole during drilling causing a sloughing of the side wall of the bore hole. This latter condition may arise even though the water entering the bore hole is being blown out of the hole as fast as it enters. If there is a substantial inflow of water or if there is a substantial flow of water past a region of the bore hole susceptible to this condition, the water passing that region of the bore hole may cause a sloughing of the side wall.

The addition of foam forming materials to the air flow when air drilling is employed in conjunction with sufficient water to provide foaming gives rise to numerous advantages in drilling operations. The water may be introduced either through a water bearing stratum being penetrated by the drill bit or, alternatively, if the hole is dry, water may be introduced from the surface of the earth through the drill stem in conjunction with the delivery of compressed air and foam forming material through the drill stem to the drill bit. In either case the water may be said to be existing in the bore hole, and drilling operations are described in U.S. Pat. No. 3,130,798.

The amount of the compositions of the invention to be employed as a corrosion inhibitor can vary widely depending upon particular compounds, the particular system, the amounts of oxygen present, etc. I may employ concentrations of from about 0.5 to 5,000 ppm, such as from about 4 to 4,000 ppm, for example from about 20 to 2,000 ppm, but preferably from about 100 to 1,000 ppm. The optimum amount, to be determined in each instance, which will depend on function and economics, can be lesser or greater than the above amounts under proper conditions.

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas wells which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formation and/or substantial quantities of oil can no longer be obtained by the usual pumping methods, various processes are sometimes used for the treatment of the oil-bearing formation in order to increase the flow of the oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system." If the water is recirculated in a closed system without substantial aeration, the secondary recovery method is referred to herein as a "closed water flooding system."

Because of the corrosive nature of oil field brines, to economically produce oil by water flooding, it is necessary to prevent or reduce corrosion since corrosion increases the cost thereof by making it necessary to repair and replace such equipment at frequent intervals.

I have now discovered a method of preventing corrosion in systems containing a corrosive aqueous media, and most particularly in systems containing brines, which is characterized by employing the compositions of this invention.

I have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances, therefore, the salt water is disposed of by injecting the water into permeable low pressure strata below the fresh water level. The formation into which the water is injected is not the oil producing formation and this type of disposal is defined as salt water disposal or waste disposal. The problems of corrosion of equipment are analogous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of the compound of this invention, sufficient to prevent corrosion, in concentrations of about 10 ppm to 10,000 ppm, or more, for example, about 50 to 5,000 ppm, but preferably about 15 to 1,500 ppm. The upper limiting amount of the compounds is determined by economic considerations. Since the success of a water flooding operation manifestly depends upon its total cost being less than the value of the additional oil recovered from the oil reservoir, it is quite important to use as little as possible of these compounds consistent with optimum corrosion inhibition. Optimum performance is generally obtained employing about 1,000 ppm. Since these compounds are themselves inexpensive and are used in low concentrations, they enhance the success of a flood operation by lowering the cost thereof.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example, five spot flooding, peripheral flooding, etc., and in conjunction with other secondary recovery methods.

Corrosion tests were made using sand blasted 1020 mild steel coupons monitored by a polarization resistance meter, a PAIR instrument described in U.S. Pat. No. 3,406,101. These tests were made in cylindrical containers of 1,500 cc volume with provision for constant stirring by means of a motor driven impeller. A thermostatically controlled immersion heater maintained an average temperature of 75° C. and an air inlet kept the fluids constantly saturated with air. Between each test the cylinder was cleaned with steam, benzene, acetone and thoroughly washed with clean water. Results of these corrosion tests made in various aqueous environments are shown in the following Table.

Protection is calculated in the usual manner from corrosion rate ($R_1$) of fluids without inhibitor and corrosion rate ($R_2$) in presence of particular inhibitor according to the formula $$\frac{R_1 - R_2}{R_1} \times 100 = \text{Percent protection.}$$

Corrosion results in aerated laboratory brine (4.2% NaCl, 1.7% Mg Cl$_2$, 0.15 CaCl$_2$, 0.09% Na$_2$SO$_4$ pH 6.0)

| Compound | Concentration | Corrosion Rate mils/year (MPY) Test Compound | Blank Corrosion Rate | % Protection |
| --- | --- | --- | --- | --- |
| Example 4 | 1000 ppm | 5.8 | 78 | 92 |
| Example 5 | 1000 ppm | 8 | 80 | 90 |
| Example 7 | 2000 ppm | 10 | 80 | 87 |
| Example 15 | 1000 ppm | 20 | 80 | 75 |
| Example 19 | 1000 ppm | 20 | 78 | 74 |

USE IN ACID SYSTEMS

The compounds of this invention can also be employed as corrosion inhibitors for acid systems, for example as illustrated by the pickling of ferrous metals, the treatment of calcareous earth formations, etc., as described in the following sections.

USE AS PICKLING INHIBITORS

This phase of the invention relates to pickling. More particularly, the invention is directed to a pickling composition and to a method of pickling ferrous metal. The term "ferrous metal" as used herein refers to iron, iron alloys and steel.

To prepare ferrous metal sheet, strip, etc., for subsequent processing, it is frequently desirable to remove oxide coating, formed during manufacturing, from the surface. The presence of oxide coating, referred to as "scale" is objectionable when the material is to undergo subsequent processing. Thus, for example, oxide scale msut be removed and a clean surface provided if satisfactory results are to be obtained from hot rolled sheet and strip in any operation involving deformation of the product. Similarly, steel prepared for drawing must possess a clean surface and removal of the oxide scale therefrom is essential since the scale tends to shorten drawing-die life as well as destroy the surface smoothness of the finished product. Oxide removal from sheet or strip is also necessary prior to coating operations to permit proper alloying or adherence of the coating to the ferrous metal strip or sheet. Prior to cold reduction, it is necessary that the oxide formed during hot rolling be completely removed to preclude surface irregularities and enable uniform reduction of the work.

The chemical process used to remove oxide from metal surfaces is referred to as "pickling." Typical pickling processes involve the use of aqueous acid solutions, usually inorganic acids, into which the metal article is immersed. The acid solution reacts with the oxides to form water and a salt of the acid. A common problem in this process is "overpickling" which is a condition resulting when the ferrous metal remains in the pickling solution after the oxide scale is removed from the surface and the pickling solution reacts with the ferrous base metal. An additional difficulty in pickling results from the liberated hydrogen being absorbed by the base metal and causing hydrogen embrittlement. To overcome the aforementioned problems in pickling, it has been customary to add corrosion inhibitors to the pickling solution.

The present invention avoids the above-described problems in pickling ferrous metal articles and provides a pickling composition which minimizes corrosion, overpickling and hydrogen embrittlement. Thus the pickling inhibitors described herein not only prevent excessive dissolution of the ferrous base metal but effectively limit the amount of hydrogen absorption thereby during pickling. According to the invention, a pickling composition for ferrous metal is provided which comprises a pickling acid such as sulfuric or hydrochloric acid and a small but effective amount of the compound of this invention, for example at least about 5 ppm, such as from about 100 to 5,000 ppm, but preferably from about 500 to 1,500 ppm.

Ferrous metal articles are pickled by contacting the surface (usually by immersion in the pickling solution) with a pickling composition as described to remove oxide from their surface with minimum dissolution and hydrogen embrittlement thereof and then washing the ferrous metal to remove the pickling composition therefrom.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareous-magnesian formation can be stimulated by introducing an acid into the producing well and forcing it into the oil or gas bearing formation. The treating acid, commonly a mineral acid such as HCl, is capable of forming water soluble salts upon contact with the formation and is effective to increase the permeability thereof and augment the flow of petroleum to the producing well.

The compositions of this invention may also be added to other aqueous and/or oxygenated systems such as steam generating systems, water circulating systems such as in cooling towers, in automobile radiators, in diesel locomotive engines, in boiler water, sea-water ship ballast, etc.

The amount of phosphoramidate employed in treating the corrosive systems of this invention will vary with the particular compound employed, the particular system, the solids present in the system, the degree of corrosivity of the system, etc. A minor amount of the compound is generally employed sufficient to impart corrosion protection to the system. In general one employs concentration of trace amounts such as from about 1.0 ppm to 10,000 ppm, for example from 5 to 5,000 ppm such as from 100 to 2,500 ppm, but preferably from 500 to 2,000 ppm. In practice, concentrations of $1,000 \pm 200$ ppm are employed.

I claim:

1. A process of inhibiting corrosion of metals in contact with a corrosive fluid which comprises contacting the metal surfaces with a dihydro-nitrogen heterocyclic phosphoramidate of the formula

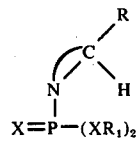

where $\overset{\frown}{N-C}$ represents a 1,2-dihydropyridine group, R is lower alkyl or phenyl and $R_1$ is lower alkyl, cyclohexyl, or phenyl and X is O or S.

2. The process of claim 1 where $\overset{\frown}{N-C}$ is

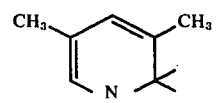

and where R is phenyl, $R_1$ is ethyl and X is O.

3. The process of claim 1 where $\overset{\frown}{N-C}$ is

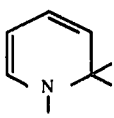

and where R is butyl, $R_1$ is methyl and X is S.

4. The process of claim 1 where N — C is

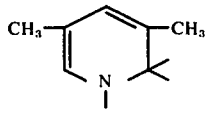

and where R is methyl, $R_1$ is ethyl and X is O.

5. The process of claim 1 where N — C is

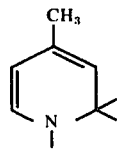

and where R is butyl, $R_1$ is ethyl and X is O.

6. The process of claim 1 where N — C is

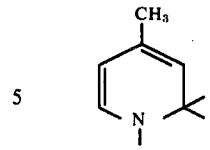

and where R is butyl, $R_1$ is methyl, and X is S.

7. The process of claim 1 where N — C is

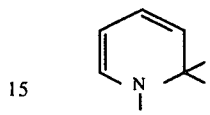

and where R is methyl, $R_1$ is isopropyl and X is O.

8. The process of claim 1 where N — C is

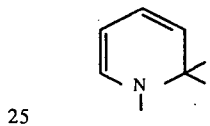

and where R is phenyl, $R_1$ is ethyl and X is O.

9. The process of claim 1 wherein the phosphoramidate is added to the corrosive fluid.

10. The process of claim 9 wherein the metal surfaces are surfaces of ferrous metals.

11. The process of claim 10 wherein the corrosive fluid is acidic.

12. The process of claim 10 wherein the corrosive fluid is a brine.

* * * * *